US012806367B2

(12) United States Patent
Vesel et al.

(10) Patent No.: US 12,806,367 B2
(45) Date of Patent: Nov. 24, 2026

(54) METHODS FOR DEPOSITION OF CHITOSAN COATING ON URINARY CATHETERS

(71) Applicant: Jozef Stefan Institute, Ljubljana (SI)

(72) Inventors: Alenka Vesel, Ljubljana (SI); Miran Mozetic, Ljubljana (SI); Gregor Primc, Ljubljana (SI); Rok Zaplotnik, Ljubljana (SI); Albert Kurincic, Kobarid (SI)

(73) Assignee: Jozef Stefan Institute, Ljubljana (SI)

( * ) Notice: Subject to any disclaimer, the term of this patent is extended or adjusted under 35 U.S.C. 154(b) by 423 days.

(21) Appl. No.: 18/460,126

(22) Filed: Sep. 1, 2023

(65) Prior Publication Data

US 2024/0207569 A1 Jun. 27, 2024

(30) Foreign Application Priority Data

Dec. 24, 2022 (EP) .................................... 22216671

(51) Int. Cl.
*A61M 25/00* (2006.01)
*A61L 29/00* (2006.01)
(Continued)

(52) U.S. Cl.
CPC ....... *A61M 25/0009* (2013.01); *A61L 29/005* (2013.01); *A61L 29/08* (2013.01);
(Continued)

(58) Field of Classification Search
CPC .......... A61M 25/0009; A61M 25/0017; A61M 2207/10; A61L 29/005; A61L 29/08;
(Continued)

(56) References Cited

FOREIGN PATENT DOCUMENTS

CN 104721890 A 6/2015
CN 104874028 A 9/2015
(Continued)

OTHER PUBLICATIONS

Vesel ("A Method for the Immobilization of Chitosan onto Urinary Catheters", Vesel et al, Int. J. Mol. Sci. 2022, 23, 15075) (Year: 2022).*

(Continued)

*Primary Examiner* — Michael G Miller
(74) *Attorney, Agent, or Firm* — Ziegler IP Law Group, LLC.

(57) ABSTRACT

The aspects of the disclosed embodiments relates to methods for optimization of the sliding properties of urinary catheters. The urinary catheters are first treated with a non-equilibrium gaseous plasma sustained in reactive gases or a mixture of a reactive gas with a noble gas. The first treatment enables a hydrophilic surface finish when oxygen is a reactive gas and an almost super-hydrophilic finish when the catheter is treated with hydrogen plasma followed by oxygen plasma. The hydrophilicity of the surface finish obtained upon the first plasma treatment is beneficial for adhering a layer of water solution of chitosan, which spreads uniformly on the entire outer surface of the catheter. The catheter with a layer of water solution of chitosan is dried and then treated with plasma containing an oxidative gas for better absorption of water by the dried chitosan film.

18 Claims, 2 Drawing Sheets

(51) Int. Cl.
*A61L 29/08* (2006.01)
*A61L 29/14* (2006.01)

(52) U.S. Cl.
CPC ......... *A61L 29/14* (2013.01); *A61M 25/0017* (2013.01); *A61L 2420/02* (2013.01); *A61M 2207/10* (2013.01)

(58) Field of Classification Search
CPC .... A61L 29/14; A61L 2420/02; A61L 29/041; A61L 29/145; A61L 29/085; A61L 2400/18
See application file for complete search history.

(56) References Cited

FOREIGN PATENT DOCUMENTS

| | | | |
|---|---|---|---|
| CN | 204684403 | U | 10/2015 |
| CN | 111420245 | A | 7/2020 |
| EP | 0808181 | A1 | 11/1997 |
| EP | 1744836 | A2 | 1/2007 |
| EP | 1846051 | A2 | 10/2007 |
| EP | 2468319 | A1 | 6/2012 |
| KR | 102235362 | B1 | 4/2021 |

OTHER PUBLICATIONS

Ahmad Asadinezhad et al., "A Physicochemical Approach to Render Antibacterial Surfaces on Plasma-Treated Medical-Grade PVC: Irgasan Coating", Plasma Processes and Polymers, 2010, pp. 504-514, WILEY-VCH Verlag GmbH & Co. KGaA, Weinheim, 11 pages.

Alenka Vesel et al., "A Method for the Immobilization of Chitosan onto Urinary Catheters", International Journal of Molecular Sciences 2022, 23, 15075. https://doi.org/10.3390/ijms232315075, 18 pages, Dec. 1, 2022, 18 pages.

Konrad Terpilowski et al., "Influence of nitrogen plasma treatment on the wettability of polyetheretherketone and deposited chitosan layers", Adv Polym Technol. 2017;00:1-13, WIley, 13 pages.

Yu Ren et al., "Influence of DBD plasma pretreatment on the deposition of chitosan onto UHMWPE fiber surfaces for improvement of adhesion anddyeing properties", Applied Surface Science 396 (2017) 1571-1579, Available online Nov. 28, 2016, 9 pages.

* cited by examiner

METHODS FOR DEPOSITION OF CHITOSAN COATING ON URINARY CATHETERS

STATEMENT REGARDING PRIOR DISCLOSURES BY THE INVENTOR OR A JOINT INVENTOR.

The inventor, Alenka Vesel, is the author of the publication "A Method for the Immobilization of Chitosan onto Urinary Catheters", International Journal of Molecular Sciences 2022, 23, 15075. https://doi.org/10.3390/ijms232315075, published on 1 Dec. 2022, 18 pages.

FIELD

The aspects of the disclosed embodiments belongs to the field of medical devices for introducing media into the body or for taking media from the body. More precisely, the aspects of the disclosed embodiments belongs to the field of catheters and methods for their production and treatment. The present aspects of the disclosed embodiments relates to methods for the deposition of a thin film of chitosan with hydrophilic character on the outer surface of urinary catheters made from polymers or polymer blends.

BACKGROUND AND THE TECHNICAL PROBLEM

Urinary catheters are medical devices used by patients to drain the bladder before, during, or after surgery, for patients having problems with urinary incontinence, urinary retention, problems with the prostate, and for patients having other health problems causing patients' inability to urinate on their own. Urinary catheters are long flexible tubes made from medical-grade polymers with appropriate mechanical properties, chemical inertness, and biocompatibility. The choice of polymers satisfying these requirements is limited to polymer blends of moderate hydrophobicity. The hydrophobicity is a drawback at any attempt to be soaked with a water solution and/or suspension of a material to be used as a coating. The coating should be approved in medical practice and should exhibit appropriate biocompatibility and hydrophilicity. The surface of the catheter must be hydrophilic to enable easier insertion into the urethra and to avoid mechanical irritation, pain, and injury of the urinary tract during its insertion leading to inflammation. Furthermore, it is also desirable that the coating has antibacterial properties since bacterial infections are one of the most frequent complications resulting from bacteria entering the bladder during the insertion of the catheter. Natural polysaccharides are among the best candidates for the coating because of their proven biocompatibility, relatively low price, and ability to be soaked with water in order to make a lubricant-like coating useful as the final surface finish. Among natural polysaccharides, alginate is a common material that exhibits excellent swelling properties. A drawback of alginate is the formation of biofilms of alginate-tolerable bacteria. Some bacteria use pure polysaccharides as a growth medium, so alginate may not be an appropriate coating for application in urinary catheters.

An excellent substitute for alginate is a bacteriostatic polysaccharide. Chitosan exhibits not only bacteriostatic but even antibacterial properties due to the presence of the amino groups on the polysaccharide chain. It is extracted from chitin, a naturally abounded polysaccharide. Chitosan is soluble in water at reasonable concentrations. The dried chitosan, however, wets slowly upon soaking with water, which may be a drawback at any attempt when the coating on a catheter should swell quickly upon wetting, for example, in a few seconds after wetting. Such a fast absorption of water is needed because a sterile packed catheter should be dry, and the wetting is performed just before using the catheter.

The use of chitosan as a catheter coating is thus limited because of two drawbacks: first, the water solution of chitosan will not adhere to the raw catheter because of the hydrophobic character of the polymer blends used for manufacturing catheters, and second, the dry chitosan exhibits the slow soaking of water and thus inadequate swelling in a reasonable time. The aspects of the disclosed embodiments aims to solve these problems. The technical problem is thus the development of a method for the treatment of catheters that will result in uniformly and efficiently coated catheters with chitosan.

PRIOR ART

Various solutions have been proposed to overcome at least one of those drawbacks. For example, CN201510170429 proposes dipping the urinary catheter into a solution containing numerous chemicals, including a variety of polysaccharides, among them also chitosan. CN201510170429 discloses a super-lubricant antibacterial catheter. In a preferred embodiment, the catheter is first coated with a chitosan antibacterial layer, followed by a hydroxypropyl cellulose lubricating layer. A similar solution is also proposed in CN204684403.

Subsequent deposition of chitosan and other coatings is also disclosed in CN104721890. The inventors disclose that chitosan has the action of reducing drug resistance and adverse effects caused by the medicinal antibacterial agent to users, hydroxypropyl cellulose and hydroxypropyl methylcellulose have lubricating action, whereas acetylcysteine has antibacterial and phlegm-reducing actions.

A catheter made from plastics and coated with a chitosan-containing lubricant is also disclosed in EP2468319. Catheters made from polyvinyl chloride were first coated by dipping into a water solution of chitosan salts, triclosan, and dicarboxylic acid; the solution also contained silver nanoparticles and at least two vitamins. Such a water solution exhibits good wetting properties, much better than a water solution of pure chitosan. After drying at room temperature in an ambient atmosphere, the coating was optionally cured by exposure to ultraviolet radiation. The nanostructured layer prevented the formation of biofilms, the development of irritation, and inflammatory states, according to EP2468319.

KR102235362 discloses a catheter with a chitosan chemostatic material that is adhered to a warped surface of a balloon. The chitosan chemostatic material is in the fabric form, including at least one external skin and one internal part. A similar catheter with the balloon is also disclosed in CN111420245, except that nano-chitosan is in the form of molecular sieves.

EP1846051A2 discloses a method for attaching chitosan to a polymer comprising: (a) providing a wettable surface of a polymer; (b) contacting a chitosan acid salt solution comprising chitosan and at least one volatile organic acid to the wettable surface of (a) to produce a chitosan-coated polymer. An option for providing a wettable surface of a polymer is plasma treatment.

EP1744836A2discloses a method for forming an active material containing a coating on a substrate, wherein the substrate is pre-treated with plasma. The active material is sprayed on the substrate, wherein the spraying is performed upon plasma conditions, i.e. the active material is introduced into the plasma discharge. Various active materials could be introduced in the plasma discharge to benefit from deposition on a substrate, including enzymes, proteins, vitamins, agrochemicals, and catalysts. The substrate may be a catheter. The long list of substrates includes chitosan.

EP0808181A1 discloses the pre-treatment of an object with a gaseous plasma sustained in a variety of gases, and coating the pre-treated surface with a solution containing a reaction product of the hyaluronic acid, or the derivative thereof, and the alkoxy silane coupling agent. In another embodiment, the plasma pre-treated object is coated with a solution containing the reaction product of the semisynthetic polymer and the alkoxy silane coupling agent, wherein the semisynthetic polymer may be an ester of chitosan. The object may be a catheter.

A common technique for increasing the wettability of polymer blends before depositing chitosan is treatment with non-equilibrium gaseous plasma. The plasma consists of reactive species such as molecular radicals and free atoms, which may bond chemically on the polymer surface, thus increasing the wettability and adhesion of chitosan [Ren Y., et al., *Influence of DBD plasma pretreatment on the deposition of chitosan onto UHMWPE fiber surfaces for improvement of adhesion and dyeing properties, Appl. Surf. Sci.* 396 (2017) 1571, Terpiłowski K., et al., *Influence of nitrogen plasma treatment on the wettability of polyetheretherketone and deposited chitosan layers,* 37 (2017) 1557]. A complex method for the treatment of medical-grade polyvinyl chloride is disclosed in [Asadinezhad A., et al., *A physicochemical approach to render antibacterial surfaces on plasma-treated medical-grade PVC: Irgasan coating, Plasma Process Polym.* 7 (2010) 504]. The samples were treated with a diffuse coplanar surface barrier discharge plasma in the air at ambient temperature and pressure, followed by radical graft copolymerization of acrylic acid onto the surface and deposition of irgasan as a potent biocide. A moderate hydrophilicity of the polyvinyl chloride with a water contact angle of 65° was reported. Plasma treatment enabled a good adhesion of the acrylic acid but was not useful for the adhesion of a chitosan film. However, the plasma used in mentioned treatments differs from the present aspects of the disclosed embodiments, particularly in the ratio between the ion and neutral radical densities.

SUMMARY

The problem of poor adhesion of the water solution of chitosan is overcome by the present aspects of the disclosed embodiments as defined in the independent claim. Preferred embodiments are defined in dependent claims. The aspects of the disclosed embodiments is based on treatment with gaseous plasma, wherein the outer surface of a catheter is subjected to a flux of reactive species and radiation. Both cause bond scission and, thus, the formation of dangling bonds. The reactive species from gaseous plasma will occupy the dangling bonds and thus interact chemically on the surface of the catheter. If reactive species are oxidative species such as O atoms or OH radicals, they will cause the formation of oxygen-containing functional groups on the catheter's surface. The plasma treatment will also cause the degradation (calcination) of any organic impurity on the catheter surface.

The essence of the method according to the aspects of the disclosed embodiments is that it comprises four key steps:

a) treatment of a polymer catheter with a non-equilibrium gaseous plasma of molecular gases,
b) deposition of a water solution or water suspension of chitosan on the plasma-treated polymer catheter prepared in step a),
c) drying the catheter with the deposited solution or suspension of chitosan prepared in step b), and
d) treatment of the chitosan-coated urinary catheter prepared in step c) with non-equilibrium gaseous plasma.

This method enables the hydrophilic character of the chitosan coating on hydrophobic raw urinary catheters and, thus, excellent lubrication properties of catheters treated according to the methods of the aspects of the disclosed embodiments. The present aspects of the disclosed embodiments discloses a four-step method for the optimal surface finish of catheters with a thin chitosan film of optimal wettability and, thus, the swelling properties which are preferred for urinary catheters made from medical-grade polymer blends.

In the first step, the catheters are treated with a low-pressure non-equilibrium gaseous plasma to make the surface hydrophilic, i.e., the water contact angle is approximately 50° or even below. The hydrophilic surface finish of the raw catheter will ensure good wetting with any liquid, particularly with polar liquids. Preferably, the hydrophilic surface finish of the catheters treated with the plasma in the first step is achieved by careful selection of the treatment parameters.

In the second step, a water solution or suspension of chitosan is applied to the catheters. The solution may be applied by dipping, spraying, or any other method. The preferred concentration of chitosan is between 1 and 5% w/v, most optimally around 2 to 2.5% w/v, as the viscoelastic properties of the solution, surface tension, as well as polydispersity index are favourable at those concentrations. After applying the water solution, the catheters are hung vertically so that the excessive solution is removed. The catheters are then dried by any method, including vacuum drying, fanning, or heating until the water evaporates. After the second step, a thin continuous film of dry chitosan with a uniform thickness is obtained. The adhesion between the chitosan film and the catheter is good because the catheters were previously treated according to the first step.

It has been noticed by the inventors that the wettability of dry chitosan on catheters is not optimal because the water contact angle is approximately 85°. Therefore, the fourth step d) is employed to make the chitosan highly wettable and thus enable rapid swelling upon contact with water. The fourth step is exposure to non-equilibrium gaseous plasma sustained in molecular gases. The inventors have surprisingly observed that even a brief plasma treatment (shorter than the treatment in step a)) leads to improved properties of polymer catheters. Preferably, treatment in step d) is performed for 0.1 to 10 seconds, most preferably 1 to 3 seconds. The chitosan film will absorb water deposited onto the sample treated with all four steps within a few seconds after the incubation of the chitosan-coated catheter with water, thus making the catheter useful for application in a quick and efficient manner.

Both plasma treatments (in the first and the fourth steps) can be performed at any pressure useful for sustaining gaseous plasma in the non-equilibrium state. Low-pressure plasma is preferred because it enables a rather uniform flux of reactive plasma species onto the entire outer surface of a catheter and because the non-equilibrium gaseous plasma does not cause significant heating of catheters during the exposure to plasma species. In a preferred embodiment, the gas pressure is between 1 and 100 Pa. Much lower pressure will make the whole process longer because of the lower flux of gaseous species. Much larger pressures will make it difficult to sustain a uniform plasma in a large volume, so uniform treating of many catheters in a batch would be difficult. Furthermore, elevated pressures will cause significant heating of the catheters during the plasma treatment.

The type of gas used for sustaining plasma is not particularly limited. Single gasses or mixtures can be used, wherein plasma treatment may be performed in a single step or sequentially. An example of the latter is treatment with hydrogen plasma followed by oxygen plasma. Both noble gases and reactive gases could be used. The residual atmosphere in a hermetically-tight vacuum chamber will contain water vapor, so when employing noble gases, the atmosphere in the vacuum chamber will be a mixture of noble gas and water vapor. Mixtures of a noble gas and a reactive gas are preferred because the large concentration of a noble gas would help spread uniform plasma throughout the vacuum chamber. Plasma in the first and the fourth step can be sustained in a reactive gas in the absence of a noble gas. The list of suitable reactive gases includes but is not limited to water vapor, oxygen, ozone, nitrogen, carbon oxides, ammonia, and mixtures of these gases, including air.

The type of discharge used for sustaining gaseous plasma is not particularly limited. Both continuous and pulsed discharges are useful. If the treatment is performed at atmospheric pressure, pulsed discharges (such as corona or dielectric barrier discharge) capable of sustaining plasma streamers are preferred. Low-pressure discharges are preferred. Radio-frequency and pulsed direct current discharges are preferred for sustaining plasma at low pressure.

The method may be used for all polymeric catheters to produce ready-to-use chitosan-coated catheters with supreme wettable properties. Usually, catheters are made of a medical-grade polyvinyl (PVC) blend and from a thermoplastic elastomer (TPE) blend, and the method is efficient for the treatment of both preferred materials. The chitosan-coated catheters are characterized in that the chitosan layer is highly wettable and the water contact angle is approximately 50° or lower, preferably 40 °±5° or lower.

SUMMARY OF THE FIGURES

Embodiments and examples illustrating the methods of the aspects of the disclosed embodiments will now be discussed with reference to the accompanying figures, which show.

DETAILED DESCRIPTION

While the methods of the aspects of the disclosed embodiments may be used for all types of polymer catheters, the usefulness is demonstrated for two types of catheters, one made from a medical-grade polyvinyl (PVC) blend and the other one from a thermoplastic elastomer (TPE) blend. These materials exhibit appropriate properties and are standardly used for the synthesis of urinary catheters. Both materials are moderately hydrophobic with a water contact angle of approximately 98° and 100° for PVC and TPE, respectively. These materials do not swell upon wetting: a water droplet will dry rather than be absorbed by the PVC or TPE blends. If immersed in water or a water solution of chitosan and pulled from the water, some randomly distributed water droplets will remain on the surface of the catheters, but the vast surface will remain dry. This is a consequence of an imbalance between the surface energy of catheters and water. If catheters are dipped into a water solution of chitosan and pulled out and dried, chitosan will be scarce and non-evenly distributed on a catheter surface. Furthermore, when a catheter previously dipped in a chitosan solution and then dried is dipped into water, the chitosan deposited on the untreated catheter will dissolute in the water. The term untreated catheters here means that they were not pretreated by any means to improve their wettability or adhesion before immersion into a water solution of chitosan The untreated catheters are, thus, impractical for application because of the high friction due to the lack of a uniform chitosan coating.

Figure 1:
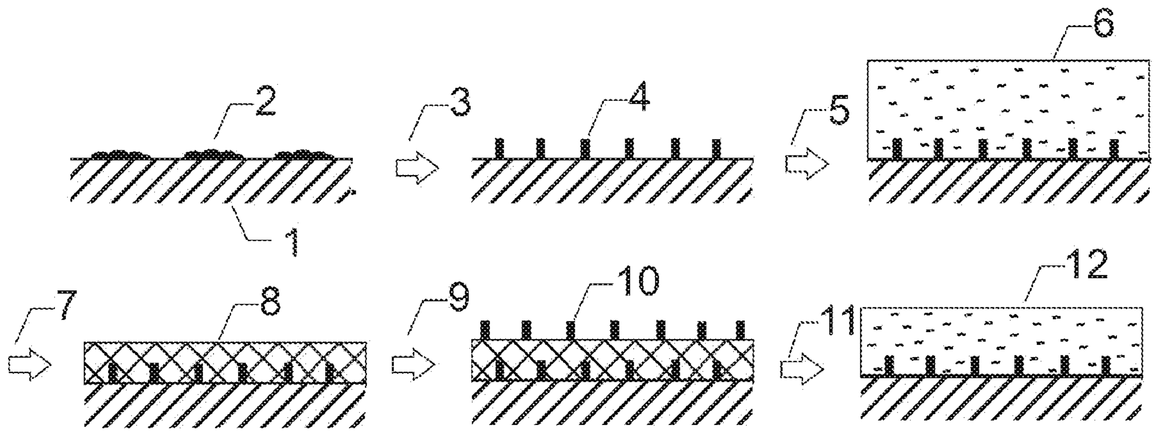
FIG. 1 a schematic of the method according to the aspects of the disclosed embodiments FIG. 2 a device for the treatment of catheters with gaseous plasma

The effect of the first step of the method, i.e., treatment with non-equilibrium oxygen plasma, is illustrated in FIG. 1. Untreated polymer catheter (1), whose surface may or may not be contaminated with impurities (2), is firstly treated with gaseous plasma (3). The gaseous plasma treatment (3) causes the removal of surface impurities (2) and causes the formation of dangling bonds on the surface of the untreated catheter (1); the dangling bonds will be occupied with oxidative species and form polar functional groups (4). The polar functional groups (4) will modify the surface wettability—the surface of the catheter treated with gaseous plasma will become polar so that the material will become hydrophilic. The water droplet will spread on the surface with a large concentration of polar functional groups (4) and assume a much lower contact angle than for the untreated catheters. The water contact angle after the first plasma treatment will depend on processing parameters and is disclosed in the examples below. The water contact angle is a simple and very reliable technique for measuring wettability. If the water contact angle is large, the wettability is poor, and vice versa. The best wettability is for an immeasurably low water contact angle.

In the second step (5), a water solution of chitosan is deposited on the catheter to form a layer (6) of water solution of chitosan, as the surface with polar functional groups (4) will attract water upon application of the water solution of chitosan (5). As a result, a thin layer of water solution of chitosan (6) will remain evenly distributed on the entire surface even after pulling the catheter out from the water solution of chitosan, as illustrated in FIG. 1. The catheter (1) with layer (6) is then dried (7), so that a solid layer of dry chitosan (8) stuck well on the surface of the catheter (1). Catheters with liquid films are not feasible for packaging, sterilization, storage, or transport, hence the drying step. The drying method is not particularly limited, but vacuum drying is preferred in one embodiment. As soon as products coated with a water-containing liquid are evacuated below the water vapor saturated pressure, the water starts boiling and desorbs from the surface, leaving a dry layer of the material initially dissolved in water, in this case, chitosan (8). The dry layer of chitosan (8) is continuous and sticks well to the surface functionalized with polar groups (4). In fact, the dry layer of chitosan (8) embraces the catheter.

The wettability of dry chitosan is sometimes inadequate, so the catheters with the solid layer of dry chitosan (8) are treated with the fourth step, i.e., with gaseous plasma (9). The properties of gaseous plasma (9) may differ from the properties of gaseous plasma (3) in the first step. Typically, the treatment time in the fourth step of plasma treatment (9) is shorter than in the first step of plasma treatment (3), preferably the second plasma treatment (9) is approximately 0.1 to 10 seconds long, which is about 10-times shorter than the first plasma treatment (3). The second plasma treatment (9) causes the formation of polar groups (10) on the surface of the solid layer of dry chitosan (8). The catheters with the solid layer of dry chitosan (8), functionalized with polar groups (10), are ready for packaging, sterilization, and transportation. The shelf time of catheters with a solid layer of dry chitosan (8) is very long, usually several years. Before application, the catheters with the solid layer of dry chitosan (8), functionalized with polar groups (10), are soaked (11) with water to form a lubricant layer (12) resembling chitosan gel.

Figure 2:
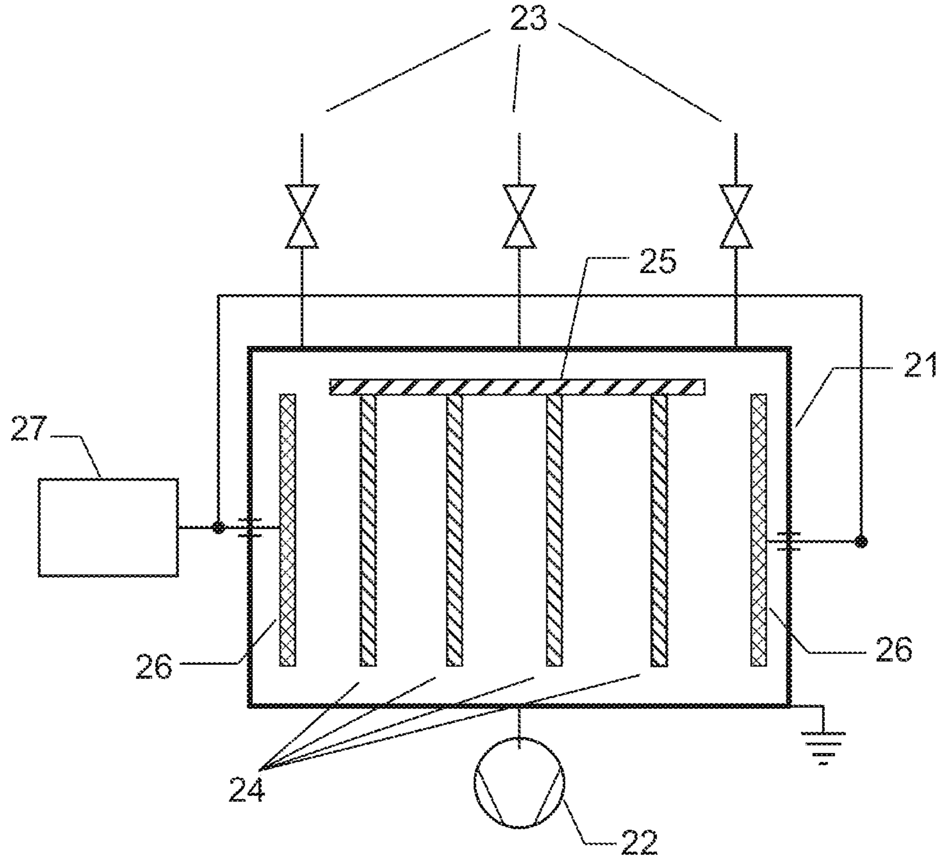

FIG. 2 shows a device useful for the treatment of catheters with gaseous plasma. The vacuum chamber (21) is hermetically tight and of vertical dimension larger than the length of catheters. The vacuum chamber (21) is pumped with one or more vacuum pumps (22). In one embodiment, the vacuum pumps (22) were roots pumps backed with a dry mechanical pump. The application of dry pumps is preferred because pumps lubricated with oil may release organic vapors, which may contaminate any product assembled into the vacuum chamber (21). The vacuum chamber (21) is equipped with one or more ports for introducing the desired gas during pumping with pumps (22). In a preferred embodiment, several ports were found useful for the proper distribution of gaseous species in the vacuum chamber (21). The ports are terminated with gas flow controllers (23), which may be replaced with needle valves. One or more gases are introduced into the vacuum chamber (21) through the flow controllers (23), for example, a noble gas, oxygen, hydrogen, nitrogen, or air. The catheters (24) are mounted on a holder (25). The catheters (24) may be evenly placed on the holder (25). Several holders (25) may be positioned in lines so that the distance between neighboring catheters is similar. In FIG. 2, only one holder (24) is shown with four catheters (25) for the sake of clarity. In one embodiment, there are several holders (24) holding several catheters (25) in the vacuum chamber (21). In a preferred embodiment, there are 10 holders (24), each holding 10 catheters, so a batch contains 100 catheters. There is at least one powered electrode (26) in the vacuum chamber (21). Two electrodes (26) are shown in the illustration in FIG. 2. The vacuum chamber (21) is grounded, and the electrodes (26) are powered with a voltage supply (27). The distance between the grounded chamber (21) and the electrode (26) is shorter than the Paschen minimum so that gaseous plasma (not shown in FIG. 2) spreads uniformly in the entire volume of the vacuum chamber (21) except within gaps between the electrode (26) and the grounded chamber (21). In a preferred embodiment, the electrodes (26) are powered with a DC pulsed power supply operating at the voltage just above the Paschen minimum. Alternatively, a radiofrequency generator may be used for sustaining plasma.

EXAMPLES

The methods of the aspects of the disclosed embodiments are further disclosed in the following examples. In all examples, a catheter or a bunch of catheters were assembled into the system shown schematically in FIG. 2. The vacuum chamber (21) was evacuated to the ultimate pressure using a roots vacuum pump backed with a dry mechanical fore pump. The nominal pumping speed of the roots pump was 600 $m^3$/h. The fore pump was a scroll pump with a nominal pumping speed of 20 $m^3$/h. Gases were introduced into the vacuum chamber (21) during continuous pumping with the pumps (22). The treatments caused increased wettability. The water contact angle of untreated PVC and TPE was 98°±2°, and 100°±2°, respectively. After the first plasma treatment, the catheters were dipped in the 2% w/w water solution of chitosan and dried. The second plasma treatment was performed according to step 3 shown in FIG. 1. The second plasma treatment was always performed using oxygen plasma with the ratio between the ion density ($O_2^{30}$) and neutral oxygen atom (O) densities of at most $10^{-5}$, usually approximately $10^{-6}$. Such a small ratio that is not commonly used was unexpectedly found beneficial for rapid hydrophilization of the chitosan coating.

Example 1: A Catheter Made from PVC Blend, the First Step Using Oxygen Plasmas PVC catheters were mounted in a plasma reactor, shown schematically in FIG. 2. The reactor was pumped down to the ultimate pressure, and the pumping time was 60 s. After achieving the ultimate pressure, oxygen was introduced into the plasma reactor to achieve the pressure of 30 Pa. Plasma was sustained at the discharge power density of 6 kW $m^{-3}$. The plasma treatment time in the first step was 60 s. The wettability improved after the plasma treatment in the first step because the water contact angle dropped to 52°±4°. Such a moderately low water contact angle was observed on the entire surface of the catheter. After dipping in the water solution of chitosan and drying, a layer of chitosan was embracing the PVC catheter, which was proved by XPS and FTIR analyses. The water contact angle on the chitosan layer embracing the PVC catheter was 90°±2°. The chitosan-coated catheters were placed in the reactor in FIG. 2 again and treated with oxygen plasma at the discharge power density of 6 kW $m^{-3}$ and pressure 30 Pa for 1 s, and the water contact angle was 40°±5°.

Example 2: A Catheter Made from PVC Blend, the First Step Using Subsequent Treatment with Hydrogen and Oxygen Plasmas PVC catheters were mounted in a plasma reactor, shown schematically in FIG. 2. The reactor was pumped down to the ultimate pressure, and the pumping time was 60 s. After achieving the ultimate pressure, hydrogen was introduced into the plasma reactor to achieve the pressure of 10 Pa. Hydrogen plasma was sustained at the discharge power density of 15 kW $m^{-3}$. The hydrogen plasma treatment time in the first step was 30 s. After hydrogen plasma treatment, oxygen was introduced into the reactor. Oxygen plasma was sustained at the discharge power density of 5 kW $m^{-3}$. The treatment time with oxygen plasma at 30 Pa was 2 s. The wettability improved after the hydrogen and plasma treatments because the water contact angle was 34±4°, indicating a very hydrophilic surface finish. Such a finish was observed on the entire surface of the catheter. After dipping in the water solution of chitosan and drying, a layer of chitosan was embracing the PVC catheter, which was proved by XPS and FTIR analyses. The water contact angle on the chitosan layer embracing the PVC catheter was 82°±6°. The catheters were placed in the reactor in FIG. 2 again and treated with oxygen plasma at the discharge power density of 6 kW $m^{-3}$ and pressure 30 Pa for 1 s, and the water contact angle was 37°±9°.

Example 3: A Catheter Made from PVC Blend, the First Step Using Subsequent Treatment with Nitrogen and Oxygen Plasmas PVC catheters were mounted in a plasma reactor, shown schematically in FIG. 2. The reactor was pumped down to the ultimate pressure, and the pumping time was 60 s. After achieving the ultimate pressure, nitrogen was introduced into the plasma reactor to achieve the pressure of 20 Pa. Nitrogen plasma was sustained at the discharge power density of 15 kW $m^{-3}$. The nitrogen plasma treatment time in the first step was 30 s. After nitrogen plasma treatment, oxygen was introduced into the reactor. Oxygen plasma was sustained at the discharge power density of 5 kW $m^{-3}$. The treatment time with oxygen plasma at 30 Pa was 2 s. The wettability improved after the nitrogen and plasma treatments because the water contact angle was 32°±6°. Such a finish was observed on the entire surface of the catheter. After dipping in the water solution of chitosan and drying, a layer of chitosan was embracing the PVC catheter, which was proved by XPS and FTIR analyses. The water contact angle on the chitosan layer embracing the PVC catheter was 88°±3°. The catheters were placed in the reactor in FIG. 2 again and treated with oxygen plasma at the discharge power density of 6 kW $m^{-3}$ and pressure 30 Pa for 1 s, and the water contact angle was 41°±5°.

Example 4: A Catheter Made from TPE Blend, the First Step Using Oxygen Plasmas TPE catheters were mounted in a plasma reactor, shown schematically in FIG. 2. The reactor was pumped down to the ultimate pressure, and the pumping time was 60 s. After achieving the ultimate pressure, oxygen was introduced into the plasma reactor to achieve the pressure of 30 Pa. Plasma was sustained at the discharge power density of 6 KW $m^{-3}$. The plasma treatment time in the first step was 60 s. The wettability improved after the plasma treatment in the first step because the water contact angle dropped to 48°±4°. Such a moderately low water contact angle was observed on the entire surface of the catheter. After dipping in the water solution of chitosan and drying, a layer of chitosan was embracing the TPE catheter, which was proved by XPS and FTIR analyses. The water contact angle on the chitosan layer embracing the TPE catheter was 97°±3°. The catheters were placed in the reactor in FIG. 2 again and treated with oxygen plasma at the discharge power density of 6 kW $m^{-3}$ and pressure 30 Pa for 1 s, and the water contact angle was 34°±5°.

Example 5: A Catheter Made from TPE Blend, the First Step Using Subsequent Treatment with Hydrogen and Oxygen Plasmas TPE catheters were mounted in a plasma reactor, shown schematically in FIG. 2. The reactor was pumped down to the ultimate pressure, and the pumping time was 60 s. After achieving the ultimate pressure, hydrogen was introduced into the plasma reactor to achieve the pressure of 10 Pa. Hydrogen plasma was sustained at the discharge power density of 15 kW $m^{-3}$. The hydrogen plasma treatment time in the first step was 30 s. After hydrogen plasma treatment, oxygen was introduced into the reactor. Oxygen plasma was sustained at the discharge power density of 5 KW $m^{-3}$. The treatment time with oxygen plasma at 30 Pa was 2 s. The wettability improved after the hydrogen and plasma treatments because the water contact angle was 11°±3°, indicating almost a super-hydrophilic surface finish. Such a finish was observed on the entire surface of the catheter. After dipping in the water solution of chitosan and drying, a layer of chitosan was embracing the TPE catheter, which was proved by XPS and FTIR analyses. The water contact angle on the chitosan layer embracing the TPE catheter was 69°±3°. The catheters were placed in the reactor in FIG. 2 again and treated with oxygen plasma at the discharge power density of 6 KW $m^{-3}$ and pressure 30 Pa for 1 s, and the water contact angle was 39°±7°.

Example 6: A Catheter Made from TPE Blend, the First Step Using Subsequent Treatment with Nitrogen and Oxygen Plasmas TPE catheters were mounted in a plasma reactor, shown schematically in FIG. 2. The reactor was pumped down to the ultimate pressure, and the pumping time was 60 s. After achieving the ultimate pressure, nitrogen was introduced into the plasma reactor to achieve the pressure of 20 Pa. Nitrogen plasma was sustained at the discharge power density of 15 KW $m^{-3}$. The nitrogen plasma treatment time in the first step was 20 s. After nitrogen plasma treatment, oxygen was introduced into the reactor. Oxygen plasma was sustained at the discharge power density of 5 KW $m^{-3}$. The treatment time with oxygen plasma at 30 Pa was 1 s. The wettability improved after the nitrogen and plasma treatments because the water contact angle was 39°±14°. After dipping in the water solution of chitosan and drying, a layer of chitosan was embracing the TPE catheter, which was proved by XPS and FTIR analyses. The water contact angle on the chitosan layer embracing the TPE catheter was 83°±2°. The catheters were placed in the reactor in FIG. 2 again and treated with oxygen plasma at the discharge power density of 6 KW $m^{-3}$ and pressure 30 Pa for 1 s, and the water contact angle was 39°±5°.

The examples are provided just as a few embodiments. A skilled person will be able to use other embodiments. For example, treatment times and discharge power densities could be altered. The gas pressures could also be different from those disclosed in the examples. The reactive gases could be mixed with one or more noble gases to benefit from plasma uniformity. Other reactive gases may be used in different embodiments. The concentration of chitosan in the water solution may be varied, too.

What is claimed is:

1. A method for preparation of chitosan-coated catheters comprising the following steps:

a) treatment of a polymer catheter with a non-equilibrium gaseous plasma of molecular gases, b) application of a water solution or water suspension of chitosan on the plasma-treated polymer catheter prepared in step a), c) drying the catheter with the applied solution prepared in step b), and d) treatment of the chitosan-coated urinary catheter prepared in step c) with non-equilibrium gaseous plasma.

2. The method according to claim 1, wherein the concentration of chitosan in step b) is between 1 and 5% w/v.

3. The method according to claim 1, wherein the chitosan solution is applied by dipping or spraying.

4. The method to claim 1, wherein drying is performed by vacuum drying, fanning, or heating until the water evaporates.

5. The method according to claim 1, wherein step d) is shorter than the treatment in step a).

6. The method according to claim 5, wherein treatment in step d) is performed for 0.1 to 10 seconds.

7. The method according to claim 5, wherein treatment in step d) is performed using oxygen plasma with the ratio between the ion density ($O_2$+) and neutral oxygen atom (O) densities at most $10^{-5}$.

8. The method according to claim 7, wherein the reactive gas is selected in the group comprising water vapor, oxygen, ozone, nitrogen, carbon oxides, ammonia, and mixtures of these gases, including air.

9. The method according to claim 5, wherein treatment in step d) is performed for 1 to 3 seconds.

10. The method according to claim 1, wherein the molecular gas in plasma treatments in steps a) and d) is at least one gas selected in the group of reactive gases, noble gasses and mixtures thereof.

11. The method according to claim 1, wherein plasma treatment is performed with two gases either in a single step or sequentially.

12. The method according to claim 11, wherein the first treatment with non-equilibrium gaseous plasma in step a) is performed using two different gases.

13. The method according to claim 12, wherein the two different gases include hydrogen or nitrogen or ammonia, followed by oxygen-comprising plasma.

14. The method according to claim 1, wherein the treatments with non-equilibrium gaseous plasma in steps a) and d) are performed with continuous and pulsed discharges.

15. The method according to claim 1, wherein the treatments with non-equilibrium gaseous plasma in steps a) and d) are performed at a pressure between 0.1 and 1,000 Pa.

16. The method according to claim 1, wherein the concentration of chitosan in step b) is between 2 to 2.5% w/v.

17. The method according to claim 1, wherein the treatments with non-equilibrium gaseous plasma in steps a) and d) are performed at a discharge power density between 0.1 and 100 KW $m^{-3}$.

18. The method according to claim 1, wherein the treatments with non-equilibrium gaseous plasma in steps a) and d) are performed at a pressure between 1 and 100 Pa.

* * * * *